United States Patent [19]

Kiehs et al.

[11] Patent Number: 4,689,068
[45] Date of Patent: Aug. 25, 1987

[54] ISOTHIOUREAS AND THEIR USE FOR CONTROLLING UNDESIRABLE PLANT GROWTH

[75] Inventors: Karl Kiehs, Lampertheim; Bruno Wuerzer, Otterstadt; Norbert Meyer, Ladenburg, all of Fed. Rep. of Germany

[73] Assignee: BASF Aktiengesellschaft, Ludwigshafen, Fed. Rep. of Germany

[21] Appl. No.: 825,387

[22] Filed: Feb. 3, 1986

[30] Foreign Application Priority Data

Feb. 9, 1985 [GB] United Kingdom ............... 3504452

[51] Int. Cl.⁴ .................... A01N 57/00; A01N 57/10; A01N 37/00; C07C 153/023
[52] U.S. Cl. ........................................ 71/86; 558/252; 558/256; 558/176; 558/169; 71/100; 71/87
[58] Field of Search ............... 558/252, 256, 176, 169; 71/100, 86, 87

[56] References Cited

FOREIGN PATENT DOCUMENTS 3136891 3/1983 Fed. Rep. of Germany ...... 558/252

OTHER PUBLICATIONS

Reid, Organic Chemistry of Bivalent Sulfur, vol. IV, Chemical Publishing Co., Inc., New York, 1962, p. 17.

*Primary Examiner*—Henry R. Jiles
*Assistant Examiner*—Robert C. Whittenbaugh
*Attorney, Agent, or Firm*—Keil & Weinkauf

[57] ABSTRACT

Isothioureas of the formula

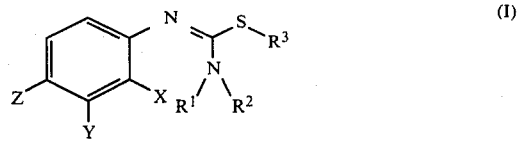

(I)

where X, Y and Z are each hydrogen, halogen, alkyl, alkoxy, haloalkyl, unsubstituted or substituted aryloxy or unsubstituted or substituted arylalkoxy, $R^1$ is alkyl, $R^2$ is alkyl or methoxy and $R^3$ is benzoyl which may be monosubstituted or disubstituted by alkyl, halogen or haloalkyl, or is a radical of the formula

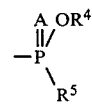

where A is oxygen or sulfur, $R^4$ is alkyl, alkoxyethyl, haloalkyl or phenyl and $R^5$ is methyl, ethyl, phenyl, alkoxy, alkoxyethoxy, haloalkoxy, phenoxy, alkylamino, dialkylamino or alkylthio, a process for their preparation, and their use for controlling undesirable plant growth.

6 Claims, No Drawings

ISOTHIOUREAS AND THEIR USE FOR CONTROLLING UNDESIRABLE PLANT GROWTH

The present invention relates to isothioureas, their preparation, herbicides which contain these compounds as active ingredients, and their use for controlling undesirable plant growth.

S-alkylated isothioureas which can be used as herbicides are disclosed in German Laid-Open Application DOS No. 3,136,891.

We have found that isothioureas of the formula

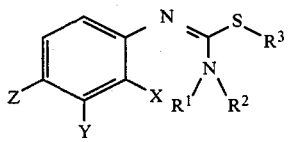

where X, Y and Z are identical or different and are each hydrogen, halogen, $C_1-C_4$-alkyl, $C_1-C_4$-alkoxy or $C_1-C_3$-haloalkyl, or are each aryl-$C_1-C_4$-alkoxy or aryloxy which is unsubstituted or substituted by halogen or $C_1-C_4$-alkyl and in which the aryl radicals may be alkylated, $R^1$ is $C_1-C_3$-alkyl, $R^2$ is $C_1-C_3$-alkyl or methoxy and $R^3$ is benzoyl which may be monosubstituted or disubstituted by $C_1-C_4$-alkyl, halogen or $C_1-C_3$-haloalkyl, or is a radical of the formula

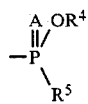

where A is oxygen of sulfur, $R^4$ is $C_1-C_4$-alkyl, $C_3-C_6$-alkoxyethyl, $C_1-C_3$-haloalkyl or phenyl, and $R^5$ is methyl, ethyl, phenyl, $C_1-C_4$-alkoxy, $C_3-C_6$-alkoxyethoxy, $C_1-C_3$-haloalkoxy, phenoxy, $C_1-C_4$-alkylamine, di-$C_1-C_4$-alkylamino or $C_1-C_4$-alkylthio, possess very good herbicidal activity and are superior to known active ingredients of similar structure.

In formula I, X, Y and Z are each hydrogen, halogen, eg. chlorine, fluorine or bromine, straight-chain or branched $C_1-C_4$-alkyl, eg. methyl, ethyl, isopropyl or tert.-butyl, straight-chain or branched $C_1-C_4$-alkoxy, eg. methoxy, ethoxy or isopropoxy, straight-chain or branched $C_1-C_3$-haloalkyl, eg. trifluoromethyl, aryl-$C_1-C_4$-alkoxy in which the aryl radical may carry $C_1-C_4$-alkyl, eg. methyl, such as 2-(4-methylphenyl)-ethoxy, 2-(4-ethylphenyl)-ethoxy, 2-(3,4-dimethylphenyl)-ethoxy, 2-(4-n-propylphenyl)-ethoxy or 2-(3,5-dimethylphenyl)ethoxy, or aryloxy which is unsubstituted or substituted by halogen or $C_1-C_4$-alkyl, eg. 4-chlorophenoxy, 1-naphthyloxy, 4-fluorophenoxy, 4-bromophenoxy, 3,4-dimethylphenoxy, 4-isopropylphenoxy, 4-tert.-butylphenoxy or 3-methyl-4-chlorophenoxy, $R^1$ is straight-chain or branched $C_1-C_3$-alkyl, eg. methyl, ethyl or isopropyl, preferably methyl, $R^2$ is straight-chain or branched $C_1-C_3$-alkyl, eg. methyl, ethyl or isopropyl, preferably methyl, or methoxy, and $R^3$ is benzoyl which may be monosubstituted or disubstituted by straight-chain or branched $C_1-C_4$-alkyl, such as methyl, ethyl, isopropyl or tert.-butyl, by halogen, such as chlorine, fluorine or bromine or by $C_1-C_3$-haloalkyl, such as trifluoromethyl or difluoromethyl, or is a radical of the formula

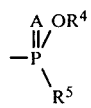

where A is oxygen or sulfur, $R^4$ is straight-chain $C_1-C_4$-alkyl-, straight-chain $C_3-C_6$-alkoxyethyl or straight-chain $C_1-C_3$-haloalkyl, such as methyl, ethyl, n-butyl, n-propyl, isobutyl, sec.-butyl, 2,2,2-trichloroethyl, 2-methoxyethyl or 2-ethoxyethyl, or phenyl, and $R^5$ is methyl, ethyl, phenyl, phenoxy, straight-chain or branched $C_1-C_4$-alkoxy, straight-chain or branched $C_3-C_5$-alkoxyethoxy, straight-chain or branched $C_1-C_3$-haloalkoxy, straight-chain or branched $C_1-C_4$-alkylamino, straight-chain or branched di-$C_1-C_4$-alkylamino or straight-chain or branched $C_1-C_4$-alkylthio, such as methoxy, ethoxy, n-butoxy, n-propylthio, isopropylthio, 2-methoxyethoxy, 2-ethoxyethoxy, 2,2,2-trichloroethoxy, isopropylamino, isobutylamino, sec.-butylamino, dimethylamino or diethylamino.

Examples of radicals $R^3$ are O,O-dimethylphosphoryl, O,O-diethylphosphoryl, O,O-di-n-propylphosphoryl, O,O-di-n-butylphosphoryl, O,O-dimethylthiophosphoryl, O,O-diethylthiophosphoryl, O,O-di-n-propylthiophosphoryl, O,O-di-n-butylthiophosphoryl, O-methyl-S-n-propyl-thiophosphoryl, O-ethyl-S-n-propylthiophosphoryl, O-methyl-S-isobutylthiophosphoryl, O-methyl-S-sec.-butylthiophosphoryl, O-ethyl-S-isobutylthiophosphoryl, O-ethyl-S-n-butylthiophosphoryl, O-ethyl-S-sec.-butylthiophosphoryl, O,O-bis-methoxyethylphosphoryl, O,O-bismethoxyethylthiophosphoryl, O,O-bisethoxy-ethylthiophosphoryl, O,O-bis-ethoxyethylphosphoryl, O,O-bis-propoxyethylthiophosphoryl, bis-isopropoxyethylphosphoryl, O-methyl-N-ethylamidophosphoryl, O-ethyl-N-ethylamidophosphoryl, O-methyl-N-isopropylamidophosphoryl, O-methyl-N-n-propylamido-phosphoryl, O-ethyl-N-n-propylamidophosphoryl, O-ethyl-N-isopropylamidophosphoryl, O-ethyl-N-iSObutylamidophosphoryl, O-ethyl-N-sec.-butylamidophosphoryl, O-methyl-N,N-dimethylamidophosphoryl, O-ethyl-N,N-dimethylamidophosphoryl, O-methyl-N,N-diethylamidophosphoryl, O-ethyl-N,N-diethylamidophosphoryl, O-methyl-N,N-di-n-propylamidophosphoryl, O-ethyl-N,N-di-n-propylamidophosphoryl, O-methyl-N,N-di-n-butylamidophosphoryl, O,O-diphenylphosphoryl, O,O-diphenylthiophosphoryl, O,O-bis-trichloroethylphosphoryl, O,O-bis-trichloroethylthiophosphoryl, O-methylmethylphosphonyl, O-ethyl-methylphosphonyl, O-methylethylphosphonyl, O-methyl-phenylphosphonyl, O-ethyl-phenylphosphonyl, O-ethoxyethyl-phenylphosphonyl, O-isopropyl-phenylphosphonyl, benzoyl, 3,4-dichlorobenzoyl, 3,5-dichlorobenzoyl, 4-bromobenzoyl, 4-fluorobenzoyl, 2-fluorobenzoyl, 3-methylbenzoyl, 4-methylbenzoyl, 3,4-dimethylbenzoyl, 2-chloro-4-trifluoromethylbenzoyl, 4-trifluoromethylbenzoyl, 3-trifluoromethylbenzoyl, 2,4-dichlorobenzoyl, 3,6-dichlorobenzoyl and 2-chlorobenzoyl.

The isothioureas of the formula I are obtained by reacting a chloroformamidine of the formula

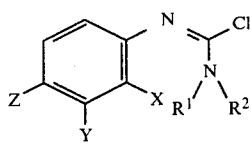
(II)

where X, Y, Z, $R^1$ and $R^2$ have the above meanings, with a thio acid of the formula $$R^3-SH \qquad (III)$$

where $R^3$ has the above meanings, in the presence of an acid acceptor.

The chloroformamidines of the formula II can be obtained by reacting a trisubsituted urea or thiourea with a chlorinating agent, such as $PCl_5$ or $COCl_2$ (Houben-Weyl, Methoden der org. Chemie, Vol. E 4, page 555 et seq. (1983)). If $R^1$ and $R^2$ in the chloroformamidines of the formula II are each alkyl, preferably methyl, it may be advantageous to prepare the chloroformamidines starting from phosgeneiminium chloride, according to the equation below.

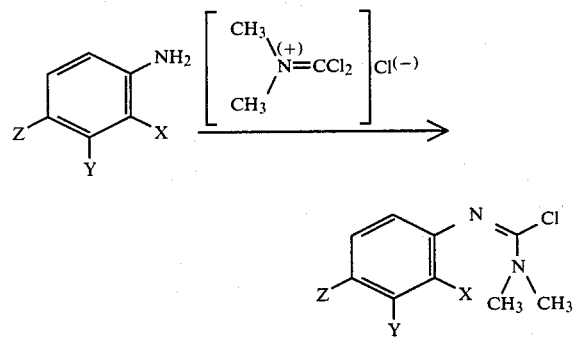

(Houben-Weyl, Methoden der org. Chemie, Vol. E 4, page 558 (1983)).

The thio acids of the formula III are used in the form of their salts (for example alkali metal, alkaline earth metal or ammonium salts), or the free acids are used together with a suitable inorganic or organic acid acceptor. These preferably include tertiary amines, alkaline earth metal compounds, ammonium compounds and alkali metal compounds, as well as mixtures of these. However, zinc compounds may also be used. Examples of these are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc acetate, sodium formate, sodium acetate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, diisopropylethylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N-methylpyrrolidone, N-ethylpyrrolidone, N-methylpiperidine, N-ethylpiperidine, N-methylpyrrolidine, N-ethylpyrrolidine, N-methylimidazole, N-ethylimidazole, N-methylpyrrole, N-methylmorpholine, N-ethylmorpholine, N-methylhexamethyleneimine, N-ethylhexamethyleneimine, pyridine, quinoline, α-picoline, β-picoline, isoquinoline, pyrimidine, acridine, N,N,N',N'-tetramethylethylenediamine, N,N,N',N'-tetraethylethylenediamine, quinoxaline, quinazoline, N-propyldiisopropylamine, N,N'-dimethylcyclohexylamine, 2,6-lutidine, 2,4-lutidine, trifvrylamine and triethylenediamine.

The reaction of the chloroformamidine II with the thio acid III is carried out using roughly stoichiometric amounts of the substances, ie. a ratio of compound III to compound II of about 1.0:1.0 to 1.4:1.0.

Advantageously, the reaction is carried out in an inert solvent. Examples of suitable solvents are halohydrocarbons, in particular chlorohydrocarbons, eg. tetrachloroethylene, 1,1,2,2- or 1,1,1,2-tetrachloroethane, dichloropropane, methylene chloride, dichlorobutane, chloroform, chloronaphthalene, dichloronaphthalene, carbon tetrachloride, 1,1,1- or 1,1,2-trichloroethane, trichloroethylene, pentachloroethane, o-, m- or p-difluorobenzene, 1,2-dichloroethane, 1,1-dichloroethane, 1,2-cis-dichloroethylene, chlorobenzene, fluorobenzene, bromobenzene, iodobenzene, o-, p- or m-dichlorobenzene, o-, p- or m-dibromobenzene, o-, m- or p-chlorotoluene or 1,2,4-trichlorobenzene; ethers, eg. ethyl propyl ether, n-butyl ethyl ether, di-n-butyl ether, diisobutyl ether, diisoamyl ether, diiSopropyl ether, anisole, phenetole, cyclohexyl methyl ether, diethyl ether, ethylene glycol dimethyl ether, tetrahydrofuran, dioxane, thioanisole or β,β'-dichlorodiethyl ether; nitrohydrocarbons, such as nitromethane, nitroethane, nitrobenzene, o-, m- or p-chloronitrobenzene or o-nitrotoluene; nitriles, such as acetonitrile, butyronitrile, isobutyronitrile, benzonitrile or m-chlorobenzonitrile; aliphatic and cycloaliphatic hydrocarbons, eg. heptane, pinane, nonane, o-, m- or p-cymene, gasoline fractions boiling within a range from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane or octane; esters, eg. ethyl acetate or isobutyl acetate; ketones, eg. acetone or methyl ethyl ketone, and mixtures of these. Advantageously, the solvent is used in an amount of from 100 to 2000, preferably from 200 to 700, % by weight, based on the starting materials.

The reaction temperature can be varied within a fairly wide range. In general, the reaction is carried out at from about 0° to about 120° C., preferably from 20° to 50° C. Since the reaction is exothermic in some cases, it may be advantageous to cool externally at the beginning of the reaction.

To complete the reaction, the mixture is stirred for a further 15 minutes to 24 hours, preferably from 1 hour to 5 hours, after which, depending on the solvent, the mixture is washed directly with water or the solvent is distilled off, and the residue is treated in a water-immiscible solvent and water. In any case, after phase separation has taken place the organic layer is evaporated down, and the product obtained as the residue can, if required, be purified by recrystallization or column chromatography.

The Examples which follow illustrate the preparation of the isothioureas of the formula I.

EXAMPLE 10.4 g (0.05 mole) of phosphorus pentachloride and 11.6 g (0.05 mole) of N,N-dimethyl-N'-(3,4-dichlorophenyl)-urea in 74 ml of toluene are refluxed for 3 hours, and the volatile components are distilled off under 0.13 mbar to give 12.6 g of N,N-dimethyl-N'-(3,4-dichlorophenyl)-chloroformamidine in the form of an oil; $n_D^{25}$: 1.6133.

|  | C | H | N | Cl |
|---|---|---|---|---|
| Calculated | 42.97 | 3.6 | 11.1 | 42.28 |
| Found | 42.7 | 3.7 | 10.6 | 42.7 |

8.4 g (0.03 mole) of N,N-dimethyl-N'-(3,4-dichlorophenyl)-chloroformamidine are added dropwise, at room temperature, to 8.8 g (0.036 mole) of dimethylammonium O-ethyl-S-n-propyldithiophosphate in 75 ml of acetone. After 2 hours, the solvent is distilled off and the residue is treated with methylene chloride/water. Evaporating down the dry organic phase gives 11.6 g of N,N-dimethyl-N'-(2,4-dichlorophenyl-S-(O-ethyl-S-n-propyl-thiophosphoryl)-isothiourea as a yellow oil; $n_D^{25}$: 1.5943.

|  | C | H | N | S | Cl | P |
|---|---|---|---|---|---|---|
| Calculated | 40.5 | 5.06 | 6.7 | 15.4 | 17.1 | 7.4 |
| Found | 40.9 | 5.0 | 6.8 | 14.9 | 18.6 | 7.1 |

The following isothioureas of the formula I can be prepared by a similar method:

| Compound | R$^1$ | R$^2$ | R$^3$ | X | Y | Z | M.p. [°C.]/$n_n^{20}$ |
|---|---|---|---|---|---|---|---|
| 1 | CH$_3$ | CH$_3$ | (C$_2$H$_5$O)$_2$PS | H | Cl | Cl | 1.5988 |
| 2 | CH$_3$ | CH$_3$ | (C$_2$H$_5$O)$_2$PO | H | Cl | Cl | 1.5795 |
| 3 | CH$_3$ | CH$_3$ | (C$_2$H$_5$O)PO(S—nC$_3$H$_7$) | H | Cl | Cl | 1.5943 |
| 4 | CH$_3$ | CH$_3$ | (C$_2$H$_5$O)PO(S—nC$_3$H$_7$) | H | CF$_3$ | H | 1.5420 |
| 5 | CH$_3$ | CH$_3$ | (C$_2$H$_5$O)PO(S—nC$_3$H$_7$) | H | H | i-C$_3$H$_7$ | 1.5710 |
| 6 | CH$_3$ | CH$_3$ | (C$_2$H$_5$O)PO(S—nC$_3$H$_7$) | H | H | 2-(4-methylphenyl)-ethoxy | 1.5828 |
| 7 | CH$_3$ | OCH$_3$ | (C$_2$H$_5$O)PO(S—nC$_3$H$_7$) | H | Cl | Cl | 1.5885 |
| 8 | CH$_3$ | OCH$_3$ | (C$_2$H$_5$O)PO(S—nC$_3$H$_7$) | H | Cl | F |  |
| 9 | CH$_3$ | OCH$_3$ | (C$_2$H$_5$O)PO(S—nC$_3$H$_7$) | H | F | F |  |
| 10 | CH$_3$ | CH$_3$ | (C$_2$H$_5$O)$_2$PO | H | CF$_3$ | H | 1.5170 |
| 11 | CH$_3$ | CH$_3$ | (C$_2$H$_5$O)$_2$PO | H | H | 4-chlorophenoxy | 1.5811 |
| 12 | CH$_3$ | CH$_3$ | (C$_2$H$_5$O)$_2$PO | H | H | i-C$_3$H$_7$ | 1.5505 |
| 13 | CH$_3$ | CH$_3$ | (C$_2$H$_5$O)$_2$PO | H | H | 2-(4-methylphenyl)-ethoxy | 1.5720 |
| 14 | CH$_3$ | OCH$_3$ | (C$_2$H$_5$O)$_2$PO | H | Cl | Cl | 1.5650 |
| 15 | CH$_3$ | OCH$_3$ | (C$_2$H$_5$O)$_2$PO | H | CF$_3$ | H | 1.5155 |
| 16 | CH$_3$ | OCH$_3$ | (C$_2$H$_5$O)$_2$PO | H | Cl | CH$_3$ | 1.5572 |
| 17 | CH$_3$ | CH$_3$ | (C$_2$H$_5$O)$_2$PO | F | H | H |  |
| 18 | CH$_3$ | CH$_3$ | (C$_2$H$_5$O)$_2$PO | H | H | F |  |
| 19 | CH$_3$ | CH$_3$ | (C$_2$H$_5$O)$_2$PS | H | CF$_3$ | H | 1.5390 |
| 20 | CH$_3$ | CH$_3$ | (C$_2$H$_5$O)$_2$PS | H | Cl | OCH$_3$ | 79–81 |
| 21 | CH$_3$ | CH$_3$ | (C$_2$H$_5$O)$_2$PS | H | H | i-C$_3$H$_7$ | 1.5710 |
| 22 | CH$_3$ | CH$_3$ | (C$_2$H$_5$O)$_2$PS | H | H | 2-(4-methylphenyl)-ethoxy | 1.5870 |
| 23 | CH$_3$ | OCH$_3$ | (C$_2$H$_5$O)$_2$PS | H | Cl | Cl | 1.5878 |
| 24 | CH$_3$ | OCH$_3$ | (C$_2$H$_5$O)$_2$PS | H | CF$_3$ | H | 1.5350 |
| 25 | CH$_3$ | OCH$_3$ | (C$_2$H$_5$O)$_2$PS | H | Cl | CH$_3$ | 1.5820 |
| 26 | CH$_3$ | OCH$_3$ | (C$_2$H$_5$O)$_2$PS | H | H | 2-(4-methylphenyl)-ethoxy | 1.5848 |
| 27 | CH$_3$ | OCH$_3$ | (C$_2$H$_5$O)$_2$PS | F | H | F |  |
| 28 | CH$_3$ | OCH$_3$ | (C$_2$H$_5$O)$_2$PS | H | H | t-C$_4$H$_9$ |  |
| 29 | CH$_3$ | CH$_3$ | C$_2$H$_5$OPO(NH—i-C$_3$H$_7$) | H | Cl | Cl | 1.5768 |
| 30 | CH$_3$ | CH$_3$ | C$_2$H$_5$OPO(NH—i-C$_3$H$_7$) | H | CF$_3$ | H | 93–95 |
| 31 | CH$_3$ | CH$_3$ | C$_2$H$_5$OPO(NH—i-C$_3$H$_7$) | H | H | 4-chlorophenoxy | 1.5900 |
| 32 | CH$_3$ | CH$_3$ | C$_2$H$_5$OPO(NH—i-C$_3$H$_7$) | H | H | i-C$_3$H$_7$ | 1.5523 |
| 33 | CH$_3$ | OCH$_3$ | C$_2$H$_5$OPO(NH—i-C$_3$H$_7$) | H | Cl | Cl | 1.5628 |
| 34 | CH$_3$ | OCH$_3$ | C$_2$H$_5$OPO(NH—i-C$_3$H$_7$) | H | CF$_3$ | H | 1.5188 |
| 35 | CH$_3$ | OCH$_3$ | C$_2$H$_5$OPO(NH—i-C$_3$H$_7$) | H | H | 2-(4-methylphenyl)-ethoxy | 1.5745 |
| 36 | CH$_3$ | CH$_3$ | C$_2$H$_5$OPO[N(CH$_3$)$_2$] | H | Cl | Cl | 1.5860 |
| 37 | CH$_3$ | CH$_3$ | C$_2$H$_5$OPO[N(CH$_3$)$_2$] | H | CF$_3$ | H | 1.5261 |
| 38 | CH$_3$ | OCH$_3$ | C$_2$H$_5$OPO[N(CH$_3$)$_2$] | H | Cl | Cl | 1.5738 |
| 39 | CH$_3$ | OCH$_3$ | C$_2$H$_5$OPO[N(CH$_3$)$_2$] | H | H | i-C$_3$H$_7$ |  |
| 40 | CH$_3$ | OCH$_3$ | C$_2$H$_5$OPO[N(CH$_3$)$_2$] | F | H | F |  |
| 41 | CH$_3$ | CH$_3$ | (n-C$_4$H$_9$O)$_2$PS | H | Cl | Cl | 1.5712 |
| 42 | CH$_3$ | CH$_3$ | (n-C$_4$H$_9$O)$_2$PS | H | CF$_3$ | H |  |
| 43 | CH$_3$ | CH$_3$ | (n-C$_4$H$_9$O)$_2$PS | H | F | F |  |
| 44 | CH$_3$ | CH$_3$ | (n-C$_4$H$_9$O)$_2$PS | H | H | 4-chlorophenoxy | 1.5810 |
| 45 | CH$_3$ | CH$_3$ | (C$_2$H$_5$OCH$_2$CH$_2$O)$_2$PS | H | Cl | Cl | 1.5840 |
| 46 | CH$_3$ | CH$_3$ | (C$_2$H$_5$OCH$_2$CH$_2$O)$_2$PS | H | CF$_3$ | H | 1.5283 |
| 47 | CH$_3$ | CH$_3$ | (C$_2$H$_5$OCH$_2$CH$_2$O)$_2$PS | H | H | i-C$_3$H$_7$ | 1.5510 |
| 48 | CH$_3$ | OCH$_3$ | (C$_2$H$_5$OCH$_2$CH$_2$O)$_2$PS | H | Cl | Cl | 1.5640 |
| 49 | CH$_3$ | OCH$_3$ | (C$_2$H$_5$OCH$_2$CH$_2$O)$_2$PS | H | CF$_3$ | H | 1.5228 |
| 50 | CH$_3$ | CH$_3$ | CH$_3$OPO(i-C$_4$H$_9$NH) | H | Cl | Cl | 1.5788 |
| 51 | CH$_3$ | OCH$_3$ | CH$_3$OPO(i-C$_4$H$_9$NH) | H | Cl |  |  |
| 52 | CH$_3$ | OCH$_3$ | CH$_3$OPO(i-C$_4$H$_9$NH) | H | CF$_3$ | H |  |
| 53 | CH$_3$ | CH$_3$ | CH$_3$OPO(i-C$_4$H$_9$NH) | H | CF$_3$ | H |  |
| 54 | CH$_3$ | CH$_3$ | CH$_3$OPO(i-C$_4$H$_9$NH) | H | H |  |  |
| 55 | CH$_3$ | CH$_3$ | (CCl$_3$CH$_2$O)$_2$PS | H | Cl | Cl | 140–143 |
| 56 | CH$_3$ | OCH$_3$ | (CCl$_3$CH$_2$O)$_2$PS | H | Cl | Cl | 105–107 |
| 57 | CH$_3$ | OCH$_3$ | (CCl$_3$CH$_2$O)$_2$PS | H | CF$_3$ | H | 1.5525 |
| 58 | CH$_3$ | CH$_3$ | C$_2$H$_5$OPS(C$_6$H$_5$) | H | Cl | Cl | 1.6400 |
| 59 | CH$_3$ | CH$_3$ | C$_2$H$_5$OPS(C$_6$H$_5$) | H | CF$_3$ | H | 1.5899 |
| 60 | CH$_3$ | CH$_3$ | C$_2$H$_5$OPS(C$_6$H$_5$) | H | H | i-C$_3$H$_7$ |  |

-continued

| Compound | $R^1$ | $R^2$ | $R^3$ | X | Y | Z | M.p. [°C.]/$n_D^{20}$ |
|---|---|---|---|---|---|---|---|
| 61 | $CH_3$ | $CH_3$ | $C_2H_5OPS(C_6H_5)$ | H | H | 4-chlorophenoxy | |
| 62 | $CH_3$ | $CH_3$ | $C_2H_5OPS(C_6H_5)$ | H | H | 4-methylphenoxy | |
| 63 | $CH_3$ | $CH_3$ | $(CH_3O)_2PS$ | H | Cl | Cl | 83–85 |
| 64 | $CH_3$ | $CH_3$ | $(C_6H_5O)_2PS$ | H | Cl | Cl | 1.6170 |
| 65 | $CH_3$ | $CH_3$ | $(C_6H_5O)_2PS$ | H | H | $i\text{-}C_3H_7$ | |
| 66 | $CH_3$ | $CH_3$ | $(C_6H_5O)_2PS$ | F | H | H | |
| 67 | $CH_3$ | $CH_3$ | $(CH_3O)_2PO$ | H | Cl | Cl | |
| 68 | $CH_3$ | $CH_3$ | $(CH_3O)_2PO$ | H | H | $i\text{-}C_3H_7$ | |
| 69 | $CH_3$ | $CH_3$ | $(CH_3O)_2PO$ | H | H | 4-chlorophenoxy | |
| 70 | $CH_3$ | $OCH_3$ | $(CH_3O)_2PO$ | H | Cl | Cl | |
| 71 | $CH_3$ | $OCH_3$ | $(CH_3O)_2PO$ | H | H | $t\text{-}C_4H_9$ | |
| 72 | $CH_3$ | $CH_3$ | $C_6H_5CO$ | H | Cl | Cl | 124–125 |
| 73 | $CH_3$ | $CH_3$ | $C_6H_5CO$ | H | $CF_3$ | H | 84–85 |
| 74 | $CH_3$ | $OCH_3$ | $C_6H_5CO$ | H | Cl | Cl | |
| 75 | $CH_3$ | $OCH_3$ | $C_6H_5CO$ | H | H | $i\text{-}C_3H_7$ | |
| 76 | $CH_3$ | $OCH_3$ | $C_6H_5CO$ | H | H | 4-chlorophenoxy | |
| 77 | $CH_3$ | $CH_3$ | $3\text{-}CF_3C_6H_4CO$ | H | Cl | Cl | 131–132 |
| 78 | $CH_3$ | $OCH_3$ | $3\text{-}CF_3C_6H_4CO$ | H | $CF_3$ | H | 116–118 |
| 79 | $CH_3$ | $CH_3$ | $3,4\text{-}Cl_2C_6H_3CO$ | H | Cl | Cl | |
| 80 | $CH_3$ | $CH_3$ | $3,4\text{-}Cl_2C_6H_3CO$ | H | $CF_3$ | H | |
| 81 | $CH_3$ | $CH_3$ | $3,4\text{-}Cl_2C_6H_3CO$ | H | H | $i\text{-}C_3H_7$ | |
| 82 | $CH_3$ | $CH_3$ | $3,4\text{-}Cl_2C_6H_3CO$ | H | H | 4-chlorophenoxy | |

The isothioureas of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzne, isophorone, etc., and strongly polar solvents such as dimethylformamide, dimethyl sulfoxide, N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus day, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 29 is mixed with 10 parts by weight of N-methyl-alpha-pyrrolidone. A mixture is obtained which is suitable for application in the form of very fine drops.

II. 10 parts by weight of compound no. 1 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

III. 20 parts by weight of compound no. 22 is dissolved in a mixture consisting of 60 parts by weight of cyclohexanone, 30 parts by weight of isobutanol, 25 parts by weight of the adduct of 7 moles of ethylene oxide and 1 mole of isooctylphenol, and 5 parts by weight of the adduct of 40 moles of ethylene oxide and 1 mole of castor oil.

IV. 20 parts by weight of compound no. 6 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 80 parts by weight of compound no. 36 is well mixed with 3 parts by weight of the sodium salt of diisobutylnaphthalene-alpha-sulfonic acid, 10 parts by weight of the sodium salt of a lignin-sulfonic acid obtained from a sulfate waste liquor, and 7 parts by weight of powdered silica gel, and triturated in a hammer mill.

VI. 5 parts by weight of compound no. 50 is intimately mixed with 95 parts by weight of particulate kaolin. A dust is obtained containing 3% by weight of the active ingredient.

VII. 20 parts by weight of compound no. 36 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 36 is intimately mixed with 2 parts of the calcium salt of dodecylbenzenesulfonic acid, 2 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or herbicidal agents containing them, may be applied pre- or (preferably) postemergence. If certain crop plants tolerate the active ingredients less well, application techniques may be used in which the herbicidal agents are sprayed from suitable equipment ins such a manner that the leaves of sensitive crop plants are if possible not touched, and the agents reach the soil or the unwanted plants growing beneath the crop plants (post-directed, lay-by treatment).

The amount of active ingredient applied depends on the time of the year, the plants to be combatted and their growth stage, and varies from 0.05 to 3 kg/ha, but is preferably from 0.25 to 3.0 kg/ha.

The herbicidal action of the isothioureas of the formula I on plant growth is demonstrated in greenhouse experiments.

The vessels employed were plastic flowerspots having a volume of 300 cm³, and which were filled with a sandy loam containing about 3.0% humus. The seeds of the test plants were sown shallow, and separately, according to species.

The plants used in the experiments were *Abutilon theophrasti, Amaranthus retorflexus, Arachis hypogaea, Cassia tora, Centaurea cyanus, Chenopodium album, Desmodium tortuosum, Echinochloa crus-galli, Galium aparine, Gossypium hirsutum, Helianthus annuus, Ipomoea spp., Lamium amplexicaule, Linum ussitatissimum, Lolium multiflorum, Medicago sativa, Mercurialis annua, Nicandra physaloides, Sesbania exaltata, Sinapis alba, Solanum nigrum, Sorghum halepense,* and *Triticum aestivum*.

For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. For this treatment, either plants which had been sown directly in the pots and grown there were selected, or plants which had been grown from seedlings and were transplanted to the pots a few days before treatment. The application rates for postemergence treatment varied from ingredient to ingredient, and were for example 0.5, 1.0 or 3 kg of active ingredient per hectare. No covers were placed on the vessels in this method.

The pots were set up in the greenhouse—species from warmer areas at from 20° to 35° C., and species from moderate climates at 10° to 25° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

On preemergence application of 3.0 kg/ha, for example compounds nos. 2, 3, 19 and 29 had a considerable herbicidal action, and, at 1 kg/ha, compounds nos. 47 and 73 were selectively active in wheat and sugar beets.

TABLE 1

Herbicidal action on preemergence application of 3.0 kg/ha in the greenhouse

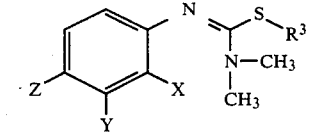

| | | | | | Test plants and % damage | | |
|---|---|---|---|---|---|---|---|
| Example no. | R³ | X | Y | Z | Echinochloa crusgalli | Lolium multifl. | Sinapis alba |
| 2 | $\underset{\underset{OC_2H_5}{\overset{\|}{-P}}}{\overset{O}{\|}}OC_2H_5$ | H | Cl | Cl | 100 | 100 | 100 |
| 3 | $\underset{\underset{OC_2H_5}{\overset{\|}{-P}}}{\overset{O}{\|}}SC_3H_7$ | H | Cl | Cl | 100 | 98 | 100 |
| 29 | $\underset{\underset{OC_2H_5}{\overset{\|}{-P}}}{\overset{O}{\|}}\overset{H}{N}-C_3H_{7i}$ | H | Cl | Cl | 95 | 100 | 100 |
| 19 | $\underset{\underset{OC_2H_5}{\overset{\|}{-P}}}{\overset{S}{\|}}OC_2H_5$ | H | CF₃ | H | 100 | 85 | 95 |

TABLE 2

Control of unwanted grasses and weeds in crops on preemergence application of compound no. 47 in the greenhouse

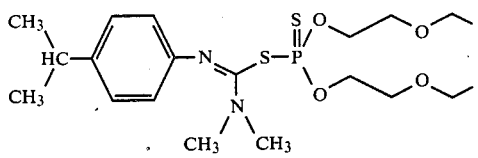

| Test plants | Damage (%); 1.0 kg/ha |
|---|---|
| Beta vulgaris | 10 |
| Triticum aestivum | 0 |
| Alopecurus myosuroides | 90 |
| Avena fatua | 95 |
| Chenopodium album | 80 |

TABLE 3

Example of selective herbicidal action of compound no. 73 on preemergence application in the greenhouse

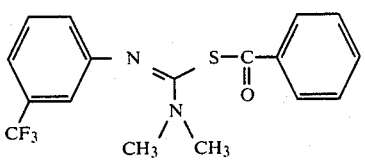

| Test plants | Damage (%); 1.0 kg/ha |
|---|---|
| Beta vulgaris | 10 |
| Triticum aestivum | 10 |
| Avena fatua | 90 |
| Viola tricolor | 80 |

On postemergence application of 3.0 kg/ha, compounds nos. 19, 30, 4, 11, 41, 45, 64, 55, 48, 59, 21, 44, 77, 73 and 5 prove to be herbicidally effective. Unwanted broad-leaved plants are selectively combatted in crop plants by application of 1.0 kg of compounds nos. 1, 29, 22, 6, 3 and 63. The crop plants were groundnuts, cotton, and sunflowers and, in the case of compound no. 3, flax alfalfa. Broadleaved weeds are selectively combatted in groundnuts and wheat by 0.5 kg/ha of compounds nos. 36 and 50.

TABLE 4

Herbicidal action on postemergence application of 3.0 kg/ha in the greenhouse

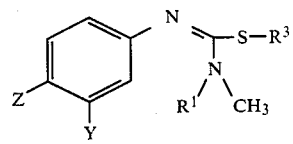

| | | | | | Test plants and % damage | | |
|---|---|---|---|---|---|---|---|
| | | | | | Centaurea cyanus | Ipomoea spp. | Lolium multiflorum |
| Ex. no. | $R^3$ | Y | Z | $R^1$ | | | |
| 19 | $-P(=S)(OC_2H_5)(OC_2H_5)$ | $CF_3$ | H | $CH_3$ | 100 | 100 | 100 |
| 30 | $-P(=O)(NC_3H_{7i})(OC_2H_5)$ H | $CF_3$ | H | $CH_3$ | 100 | 100 | 100 |
| 4 | $-P(=O)(SC_3H_{7n})(OC_2H_5)$ | $CF_3$ | H | $CH_3$ | 100 | 100 | 100 |
| 11 | $-P(=O)(OC_2H_5)(OC_2H_5)$ | H | $-O-C_6H_4-Cl$ (p) | $CH_3$ | 98 | 100 | 98 |
| 41 | $-P(=S)(OC_4H_{9n})(OC_4H_{9n})$ | Cl | Cl | $CH_3$ | 100 | 100 | 98 |
| 45 | $-P(=S)(OCH_2CH_2OC_2H_5)(OCH_2CH_2OC_2H_5)$ | Cl | Cl | $CH_3$ | 100 | 100 | 98 |

TABLE 4-continued
Herbicidal action on postemergence application of 3.0 kg/ha in the greenhouse Structure:

Phenyl ring with substituents Z (para), Y (meta), and N=C(S-R³)-N(R¹)(CH₃) group

| | | | | | Test plants and % damage | | |
|---|---|---|---|---|---|---|---|
| Ex. no. | R³ | Y | Z | R¹ | *Centaurea cyanus* | *Ipomoea* spp. | *Lolium multiflorum* |
| 64 | -P(=S)(OC₆H₅)(OC₆H₅) | Cl | Cl | CH₃ | 98 | 100 | 85 |
| 55 | -P(=S)(OCH₂CCl₃)(OCH₂CCl₃) | Cl | Cl | CH₃ | 95 | 100 | 90 |
| 48 | -P(=S)(OCH₂CH₂OC₂H₅)(OCH₂CH₂OC₂H₅) | Cl | Cl | OCH₃ | 95 | 100 | 90 |
| 59 | -P(=S)(C₆H₅)(OC₂H₅) | CF₃ | H | CH₃ | 98 | 98 | 98 |
| 21 | -P(=S)(OC₂H₅)(OC₂H₅) | H | C₃H₇ⁱ | CH₃ | 100 | 100 | 100 |
| 44 | -P(=S)(OC₄H₉ⁿ)(OC₄H₉ⁿ) | H | -O-C₆H₄-Cl | CH₃ | 100 | 100 | 95 |
| 77 | -C(=O)-C₆H₄-CF₃ | Cl | Cl | CH₃ | 90 | 100 | 95 |
| 73 | -C(=O)-C₆H₅ | CF₃ | H | CH₃ | 100 | 100 | 100 |
| 5 | -P(=O)(SC₃H₇ⁿ)(OC₂H₅) | H | C₃H₇ⁱ | CH₃ | 100 | 100 | 100 |

TABLE 5

Selective weed control with compound no. 1 on postemergence application in the greenhouse

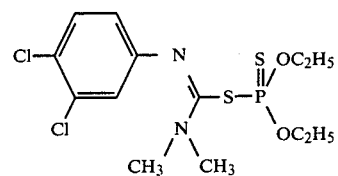

| Test plants | Damage (%); 1.0 kg/ha |
|---|---|
| Arachis hypogaea | 0 |
| Gossypium hirsutum | 8 |
| Desmodium tortuosum | 100 |
| Galium aparine | 80 |
| Lamium amplexicaule | 100 |
| Mercurialis annua | 100 |
| Nicandra physaloides | 100 |
| Sinapis alba | 90 |
| Solanum nigrum | 98 |

TABLE 6

Selective weed control with compound no. 29 on postemergence application in the greenhouse

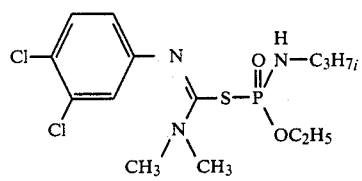

| Test plants | Damage (%); 1.0 kg/ha |
|---|---|
| Gossypium hirsutum | 0 |
| Abutilon theophrasti | 100 |
| Sorghum halepense | 90 |

TABLE 7

Selective control of broadleaved weeds in sunflowers on postemergence application in the greenhouse

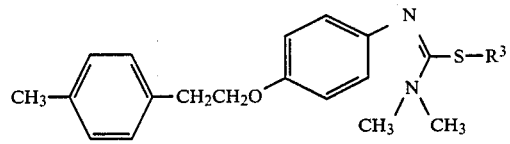

| Ex. no. | R³ | kg/ha | Helianthus annuus | Desmodium tortuosum | Lamium amplex. | Sesbania exaltata |
|---|---|---|---|---|---|---|
| 22 | 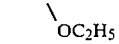 | 1.0 | 10 | 90 | 100 | 90 |

TABLE 7-continued

Selective control of broadleaved weeds in sunflowers on postemergence application in the greenhouse

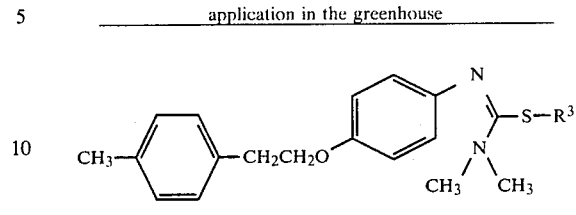

| Ex. no. | R³ | kg/ha | Helianthus annuus | Desmodium tortuosum | Lamium amplex. | Sesbania exaltata |
|---|---|---|---|---|---|---|
| 6 | O SC₃H₇ₙ \\ / -P \\ OC₂H₅ | 1.0 | 10 | 100 | 100 | 80 |

TABLE 8

Selective control of broadleaved weeds in various crops on postemergence application in the greenhouse of compound no. 3

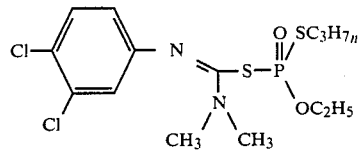

| Test plants | Damage (%); 1.0 kg/ha |
|---|---|
| Linum ussitatissimum | 0 |
| Medicago sativa | 0 |
| Chenopodium album | 100 |
| Solanum nigrum | 100 |

TABLE 9

Selective control of broadleaved weeds in groundnuts on postemergence application of compound no. 63 in the greenhouse

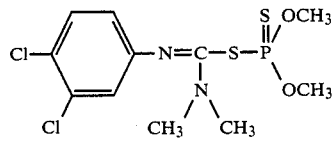

| Test plants | Damage (%); 1.0 kg/ha |
|---|---|
| Arachis hypogaea | 5 |
| Amaranthus retroflexus | 100 |
| Cassia tora | 100 |
| Desmodium tortuosum | 100 |
| Ipomoea spp. | 100 |
| Lamium amplexicaule | 100 |
| Mercurialis annua | 100 |
| Sesbania exaltata | 100 |

TABLE 10

Selective weed control in groundnuts and wheat on postemergenced application in the greenhouse

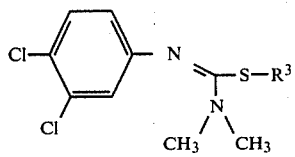

| | | | Test plants and % damage | | | | |
|---|---|---|---|---|---|---|---|
| Ex. no. | R³ | kg/ha | Arachis hypogaea | Triticum aestivum | Desmodium tortuosum | Lamium amplex. | Mercurialis annua |
| 50 | (H)O–N–CH₂–CH(CH₃)₂ / –P(OCH₃) | 0.5 | 0 | 0 | 100 | 80 | 80 |
| 36 | O–N(CH₃)₂ / –P(OC₂H₅) | 0.5 | 0 | 0 | 100 | 90 | 80 |

Compound no. 20, on postemergence application of 1.0 kg/ha, selectively combats unwanted broadleaved plants in groundnuts. Compound no. 5, applied postemergence at a rate of 0.5 kg/ha, has a selective herbicidal action in wheat.

TABLE 11

Control of broadleaved weeds in groundnuts; postemergence treatment in the greenhouse with compound no. 20

| Test plants | Damage (%); 1.0 kg/ha |
|---|---|
| Archachis hypogaea | 5 |
| Cassia tora | 90 |
| Desmodium tortuosum | 100 |
| Mercurialis annua | 100 |
| Sesbania exaltata | 100 |

TABLE 12

Selective herbicidal action of compound no. 5; postemergence application in the greenhouse

| Test plants | Damage (%); 0.5 kg/ha |
|---|---|
| Triticum aestivum | 10 |
| Chenopodium album | 100 |
| Viola tricolor | 90 |

In view of the numerous application methods possible, the isothioureas of the formula I, or agents containing them, may be used in a large number of crops for removing unwanted plants.

The following may be mentioned by way of example:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Beta vulgaris spp. esculenta | table beets; red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vetifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |

| Botanical name | Common name |
|---|---|
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes unv-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize (post-directed) |

To increase the spectrum of action and to achieve synergistic effects, the isothioureas of the formula I may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, quinolinecarboxylic acids, etc.

It may also be useful to apply the compounds of the formula I, either alone or in combination with other herbicides, in admixture with other crop protection agents, e.g., agents for combatting pests or phytopathogenic fungi or bacteria. The compounds may also be mixed with solutions of mineral salts used to remedy nutritional or trace element deficiencies. Non-phytotoxic oils and oil concentrates may also be added.

We claim:

1. An isothiourea of the formula

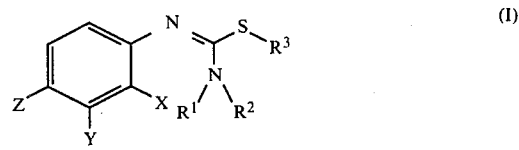

where X, Y and Z are identical or different and are each hydrogen, halogen, $C_1$–$C_4$-alkyl, $C_1$–$C_4$-alkoxy or $C_1$–$C_3$-haloalkyl, or are each phenyl or naphthyl-$C_1$–$C_4$-alkoxy or phenyloxy or naphthyloxy which is unsubstituted or substituted by halogen or $C_1$–$C_4$-alkyl and in which the phenyl or naphthyl radicals may be alkylated, $R^1$ is $C_1$–$C_3$-alkyl, $R^2$ is $C_1$–$C_3$-alkyl or methoxy and $R^3$ is benzoyl which may be monosubstituted or disubstituted by $C_1$–$C_4$-alkyl, halogen or $C_1$–$C_3$-haloalkyl, or is a radical of the formula

where A is oxygen or sulfur, $R^4$ is $C_1$–$C_4$-alkyl, $C_3$–$C_6$-alkoxyethyl, $C_1$–$C_3$-haloalkyl or phenyl, and $R^5$ is methyl, ethyl, phenyl, $C_3$–$C_6$-alkoxyethoxy, $C_1$–$C_3$-haloalkoxy, $C_1$–$C_4$-alkylamino, di-$C_1$–$C_4$-alkylamino or $C_1$–$C_4$-alkylthio.

2. An isothiourea of the formula I as set forth in claim 1, where X is hydrogen.

3. An isothiourea of the formula I as set forth in claim 1, where $R^1$ is methyl and $R^2$ is methyl or methoxy.

4. A herbicide containing an effective amount of an isothiourea of the formula I as set forth in claim 1 and conventional auxiliaries.

5. A herbicide containing an effective amount of an isothiourea of the formula I as set forth in claim 2 and conventional auxiliaries.

6. A process for combatting the growth of unwanted plants, wherein the unwanted plants or the area to be kept free from unwanted plant growth are treated with a herbicidally effective amount of an isothiourea of the formula I as set forth in claim 1.

* * * * *